(12) United States Patent
Levasseur et al.

(10) Patent No.: US 12,419,497 B2
(45) Date of Patent: *Sep. 23, 2025

(54) CONNECTED MEDICAL DEVICES

(71) Applicant: Boston Scientific Scimed, Inc., Maple Grove, MN (US)

(72) Inventors: Amy Levasseur, Holliston, MA (US); Louis J. Barbato, Franklin, MA (US); William J. Abner, Rutland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/751,481

(22) Filed: Jun. 24, 2024

(65) Prior Publication Data

US 2024/0358236 A1    Oct. 31, 2024

Related U.S. Application Data

(63) Continuation of application No. 18/361,096, filed on Jul. 28, 2023, now Pat. No. 12,042,123, which is a
(Continued)

(51) Int. Cl.
*A61B 1/00* (2006.01)
*A61B 1/005* (2006.01)
(Continued)

(52) U.S. Cl.
CPC ...... *A61B 1/00128* (2013.01); *A61B 1/00004* (2013.01); *A61B 1/00025* (2013.01);
(Continued)

(58) Field of Classification Search
None
See application file for complete search history.

(56) References Cited

U.S. PATENT DOCUMENTS 4,374,517 A    2/1983   Hagiwara
4,494,549 A    1/1985   Namba et al.
(Continued)

FOREIGN PATENT DOCUMENTS

CN    101094617 A      12/2007
EP      1602319 A1     12/2005
(Continued)

OTHER PUBLICATIONS

Machine language translation of JPH0542156 (Year: 1993).*
(Continued)

*Primary Examiner* — John P Leubecker
(74) *Attorney, Agent, or Firm* — Bookoff McAndrews, PLLC

(57) ABSTRACT

A medical system includes an insertion device including a handle, an insertion portion with at least one lumen, a port fluidly coupled to the lumen, and a connection portion. The medical system also includes a medical device including a handle, an insertion portion, and a connection portion configured to be coupled to the connection portion of the insertion device. The connection portion of the medical device is configured to be coupled to the connection portion of the insertion device to form an electronic and physical connection between the insertion device and the medical device.

20 Claims, 5 Drawing Sheets

Related U.S. Application Data continuation of application No. 16/924,258, filed on Jul. 9, 2020, now Pat. No. 11,751,753.

(60) Provisional application No. 62/874,201, filed on Jul. 15, 2019.

(51) Int. Cl.
| | | |
|---|---|---|
| *A61B 1/018* | (2006.01) | |
| *A61B 1/04* | (2006.01) | |
| *A61M 25/01* | (2006.01) | |
| *A61B 1/06* | (2006.01) | |
| *A61B 1/267* | (2006.01) | |
| *A61B 1/273* | (2006.01) | |
| *A61B 1/307* | (2006.01) | |
| *A61B 1/31* | (2006.01) | |
| *A61B 1/313* | (2006.01) | |
| *A61B 1/317* | (2006.01) | |

(52) U.S. Cl.
CPC ...... *A61B 1/00066* (2013.01); *A61B 1/00121* (2013.01); *A61B 1/00124* (2013.01); *A61B 1/00133* (2013.01); *A61B 1/018* (2013.01); *A61B 1/044* (2022.02); *A61M 25/0113* (2013.01); *A61B 1/00103* (2013.01); *A61B 1/0052* (2013.01); *A61B 1/0684* (2013.01); *A61B 1/2676* (2013.01); *A61B 1/273* (2013.01); *A61B 1/307* (2013.01); *A61B 1/31* (2013.01); *A61B 1/3132* (2013.01); *A61B 1/317* (2013.01)

(56) References Cited

U.S. PATENT DOCUMENTS

| | | | |
|---|---|---|---|
| 4,527,553 A | 7/1985 | Upsher | |
| 4,974,075 A | 11/1990 | Nakajima | |
| 6,315,712 B1 | 11/2001 | Rovegno | |
| 8,529,439 B2 | 9/2013 | Ito et al. | |
| 8,608,649 B2 | 12/2013 | McWeeney et al. | |
| 10,238,272 B2 | 3/2019 | Simmons | |
| 2002/0098732 A1 | 7/2002 | Shimizu | |
| 2002/0177373 A1 | 11/2002 | Shibata et al. | |
| 2003/0018237 A1 | 1/2003 | Okada | |
| 2003/0181789 A1 | 9/2003 | Mazzei et al. | |
| 2003/0216723 A1 | 11/2003 | Shinmura et al. | |
| 2004/0015079 A1 | 1/2004 | Berger et al. | |
| 2004/0030367 A1 | 2/2004 | Yamaki et al. | |
| 2005/0119522 A1 | 6/2005 | Okada | |
| 2005/0288547 A1 | 12/2005 | Okada | |
| 2009/0058997 A1 | 3/2009 | Kato | |
| 2009/0193160 A1 | 7/2009 | Kagawa | |
| 2010/0318100 A1 | 12/2010 | Okamoto et al. | |
| 2013/0060087 A1 | 3/2013 | Yoshida | |
| 2013/0172670 A1 | 7/2013 | Levy et al. | |
| 2014/0066711 A1 | 3/2014 | Farin et al. | |
| 2014/0107416 A1 | 4/2014 | Birnkrant | |
| 2014/0114126 A1 | 4/2014 | Dresher | |
| 2014/0213848 A1 | 7/2014 | Moskowitz et al. | |
| 2015/0057537 A1 | 2/2015 | Dillon et al. | |
| 2016/0081539 A1 | 3/2016 | Pagan | |
| 2016/0120394 A1 | 5/2016 | McGrath et al. | |
| 2017/0172402 A1 | 6/2017 | Wakabayashi | |
| 2018/0132700 A1 | 5/2018 | OuYang et al. | |
| 2020/0154982 A1 | 5/2020 | Niwa et al. | |
| 2020/0275827 A1 | 9/2020 | Weise et al. | |
| 2020/0375437 A1 | 12/2020 | Geafer et al. | |
| 2021/0145257 A1 | 5/2021 | Levinson | |

FOREIGN PATENT DOCUMENTS

| | | | |
|---|---|---|---|
| EP | 2433553 A1 | 3/2012 | |
| JP | S57117824 A | 7/1982 | |
| JP | H0542156 A | 2/1993 | |

OTHER PUBLICATIONS

International Search Report and Written Opinion issued in International Application No. PCT/US2020/041298, issued Sep. 11, 2020 (12 pages).

Japanese Office Action in corresponding Japanese Application No. 2022-502195, dated Apr. 16, 2024 (9 pages).

* cited by examiner

CONNECTED MEDICAL DEVICES

CROSS-REFERENCE TO RELATED APPLICATIONS

This patent application is a continuation of U.S. patent application Ser. No. 18/361,096, filed on Jul. 28, 2023, now U.S. Pat. No. 12,042,123, issued on Jul. 23, 2024, which is a continuation of U.S. patent application Ser. No. 16/924,258, filed on Jul. 9, 2020, now U.S. Pat. No. 11,751,753, issued on Sep. 12, 2023, which claims the benefit under 35 U.S.C. § 119 to U.S. Provisional Patent Application No. 62/874,201, filed on Jul. 15, 2019, the entirety of each of which is incorporated herein by reference.

TECHNICAL FIELD

Aspects of the present disclosure generally relate to medical systems, devices, and methods. In particular, aspects of the present disclosure relate to medical systems, devices, and methods for physically and electronically coupling medical devices.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering an insertion device to a position within the body of a patient. Additionally, many procedures involve delivering a medical device through a lumen in the insertion device. In particular, such procedures may be carried out by inserting the insertion device (e.g., a duodenoscope) into a subject's body through a surgical incision, or via a natural anatomical orifice (e.g., mouth, vagina, or rectum), and performing the procedure or operation at a target site with an auxiliary medical device (e.g., a catheter with visualization) inserted through the insertion device.

The insertion device and the medical device may each have one or more illumination devices (e.g., LEDs), visualization devices (e.g., cameras), etc., which require power sources, display devices, etc. The insertion device and the medical device may each have an umbilicus or other cables or wires in order to couple the insertion device and the medical device to power sources, controllers, user interfaces, displays, etc. The umbilicus or other cables or wires may obstruct or impede the user(s) movement during the medical procedure and/or may be accidentally twisted or disconnected during the procedure. Additionally, the insertion device and the medical device may each require separate capital devices to power, control, visualize, etc. for each of the insertion device and the medical device. The umbilicus, cables, wires, and multiple capital devices may increase the duration, costs, and risks of the medical procedure.

The devices and methods of the current disclosure may rectify some of the deficiencies described above or address other aspects of the prior art.

SUMMARY

Examples of the present disclosure relate to, among other things, systems and devices for coupling medical devices and performing one or more medical procedures with the medical devices, and related methods of use thereof. Each of the examples disclosed herein may include one or more of the features described in connection with any of the other disclosed examples.

In one example, a medical system may include an insertion device including a handle, an insertion portion with at least one lumen, a port fluidly coupled to the lumen, and a connection portion. The medical system also may include a medical device including a handle, an insertion portion, and a connection portion configured to be coupled to the connection portion of the insertion device. The connection portion of the medical device may be configured to be coupled to the connection portion of the insertion device to form an electronic and physical connection between the insertion device and the medical device.

The medical system may include one or more of the following features. The insertion portion of the medical device may be configured to be inserted through the port and through the lumen in the insertion portion of the insertion device. The connection portion of the insertion device may include a recessed port and one or more doors to movably cover the recessed port. The connection portion of the insertion device and the connection portion of the medical device may be configured to be coupled together via a friction fit. The connection portion of the medical device may include one or more extension portions that extend from the medical device to open the one or more doors and couple the medical device to the insertion device. The connection portion of the medical device may include pins, and the connection portion of the insertion device may include pin holes. The connection portion of the insertion device and the connection portion of the medical device may be coupled via a locking mechanism, and the locking mechanism may include at least two prongs with widened end portions and bendable arms. The connector portion of the insertion device may include the at least two prongs with widened end portions and bendable arms, and the connection portion of the medical device may include indentations to receive portions of the widened end portions.

The medical system may further include a control unit, and the control unit may be physically and electronically coupled to the insertion device via an umbilicus. The control unit may deliver power through the umbilicus to both the insertion device and the medical device to power one or more distal components on a distal end of the insertion portion of the insertion device and to power one or more distal components on a distal end of the insertion portion of the medical device. The insertion device may include a controller to receive signals from the distal components of the insertion device and from the distal components of the medical device. The controller may be configured to demodulate and/or compress the received signals from the distal components of the insertion device and from the distal components of the medical device. The demodulation and/or compression may include a 64-QAM carrier or orthogonal frequency division multiplexing. The insertion device and the medical device may be powered by a single umbilicus coupled to the insertion device. The single umbilicus may include a single coaxial cable.

In another aspect, a medical device may include a handle, an insertion portion with at least one lumen, a port fluidly coupled to the lumen, and a connection portion configured to be coupled to another connection portion of another medical device. The connection portion may be configured to electronically and physically couple the medical device to the another medical device.

The medical device may include one or more of the following features. The medical device may further include an umbilicus coupled to the handle and configured to couple the medical device to a control unit. The umbilicus may be configured to deliver power to the medical device to power both the medical device and the another medical device. The medical device may further include a controller configured to receive signals from distal components of both the medical device and the another medical device. The controller may be configured to demodulate and/or compress the signals received from the distal components of both the medical device and the another medical device and transmit the signals to a control unit via the umbilicus.

In yet another aspect, a method may include inserting a distal portion of an insertion portion of an insertion device into a patient body. The insertion device may include a handle coupled to the insertion portion. The method may also include coupling a handle of a medical device to the handle of the insertion device. The medical device may include an insertion portion coupled to the handle of the medical device, and coupling the handle of the medical device to the handle of the insertion device may form an electronic and physical connection between the medical device and the insertion device. The method may also include inserting the insertion portion of the medical device through a lumen of the insertion device and into the patient body and visualizing and/or performing a procedure within the patient body.

The method may include one or more of the following features. The method may also include coupling the handle of the insertion device to a control unit via an umbilicus. The insertion device may further include a controller configured to receive signals from distal components of both the insertion device and the medical device. The controller may be configured to demodulate and/or compress the signals received from the distal components of both the insertion device and the medical device and transmit the signals to the control unit via the umbilicus. The control unit may be configured to deliver power to both the insertion device and the medical device via the umbilicus.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Figure 1:
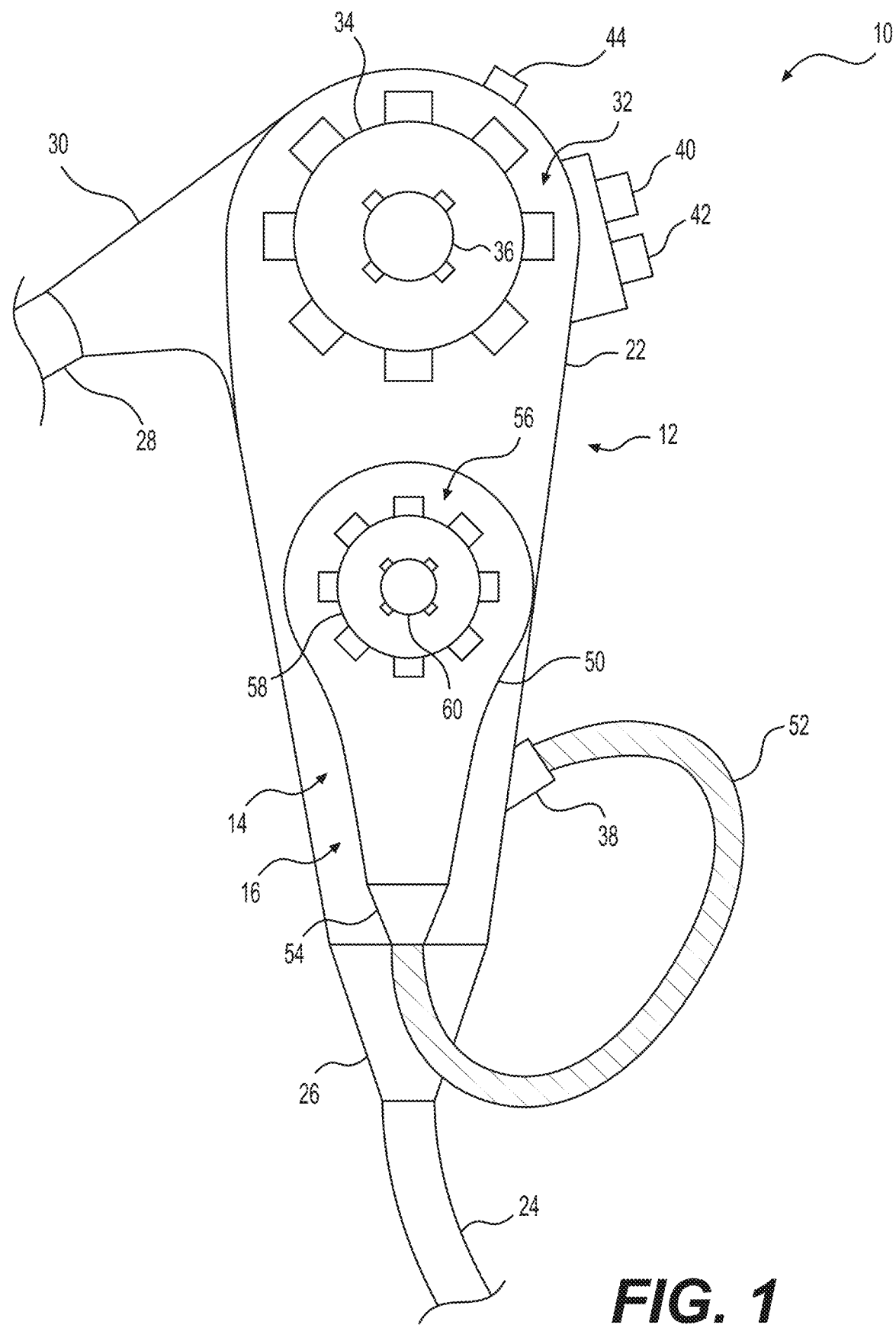
FIG. 1 illustrates an exemplary medical system including two medical devices in a coupled configuration, according to aspects of this disclosure.

Examples of the present disclosure include devices and methods for facilitating and improving the efficacy, efficiency, and/or safety of visualizing and/or manipulating tissue during a medical procedure. For example, aspects of the present disclosure may provide a user (e.g., physician, medical technician, or other medical service provider) with the ability to physically and electronically connect handles of two medical devices (e.g., an insertion device and a medical device). Aspects of the present disclosure may also provide the user with the ability to deliver the insertion device to a location within a patient's body, and also to deliver the medical device through an internal lumen of the insertion device to the location within the patient's body to, for example, visualize, resect, energize, treat, or otherwise manipulate tissue or material within a patient's body.

Embodiments of the present disclosure may relate to systems for performing various medical procedures and methods for obtaining visualization of the pancreaticobiliary system and/or any other suitable patient anatomy. Various embodiments described herein is may include single-use or disposable medical devices. More specifically, in exemplary embodiments, the medical system may be configured to deliver and position a visualization device and/or an access device, e.g., a needle-knife and/or a tome, for accessing the papilla of Vater or major papilla. The papilla of Vater generally forms the opening where the pancreatic duct and the common bile duct empty into the duodenum of the small intestine. The hepatic ducts and the gall bladder empty into the common bile duct. In general, an endoscopic or biliary procedure may require advancing a medical device to a suitable location along the biliary tree and then performing the appropriate intervention. The medical device and methods disclosed herein provide access and visualization (and a delivery system for visualization and access devices) to, among other areas, the papilla and/or pancreatico-biliary system. For example, the insertion device may be a duodenoscope that may be delivered to gain access to a papilla, and the medical device may be inserted through the duodenoscope and extended distally beyond the insertion portion of the duodenoscope and into a biliary duct.

The physical and electronic coupling of the handles of the two medical devices may further allow for the two medical devices to be connected to a single piece of capital equipment in order to power illumination devices (e.g., LEDs), visualization devices (e.g., cameras), etc. of both medical devices and to send and receive information from one or more sensors on both medical devices. Some aspects of the present disclosure may be used in performing an endoscopic, laparoscopic, arthroscopic, or other type of procedure. For example, the disclosed aspects may be used with duodenoscopes, bronchoscopes, ureteroscopes, colonoscopes, catheters, diagnostic or therapeutic tools or devices, or other types of medical devices.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figure 2:
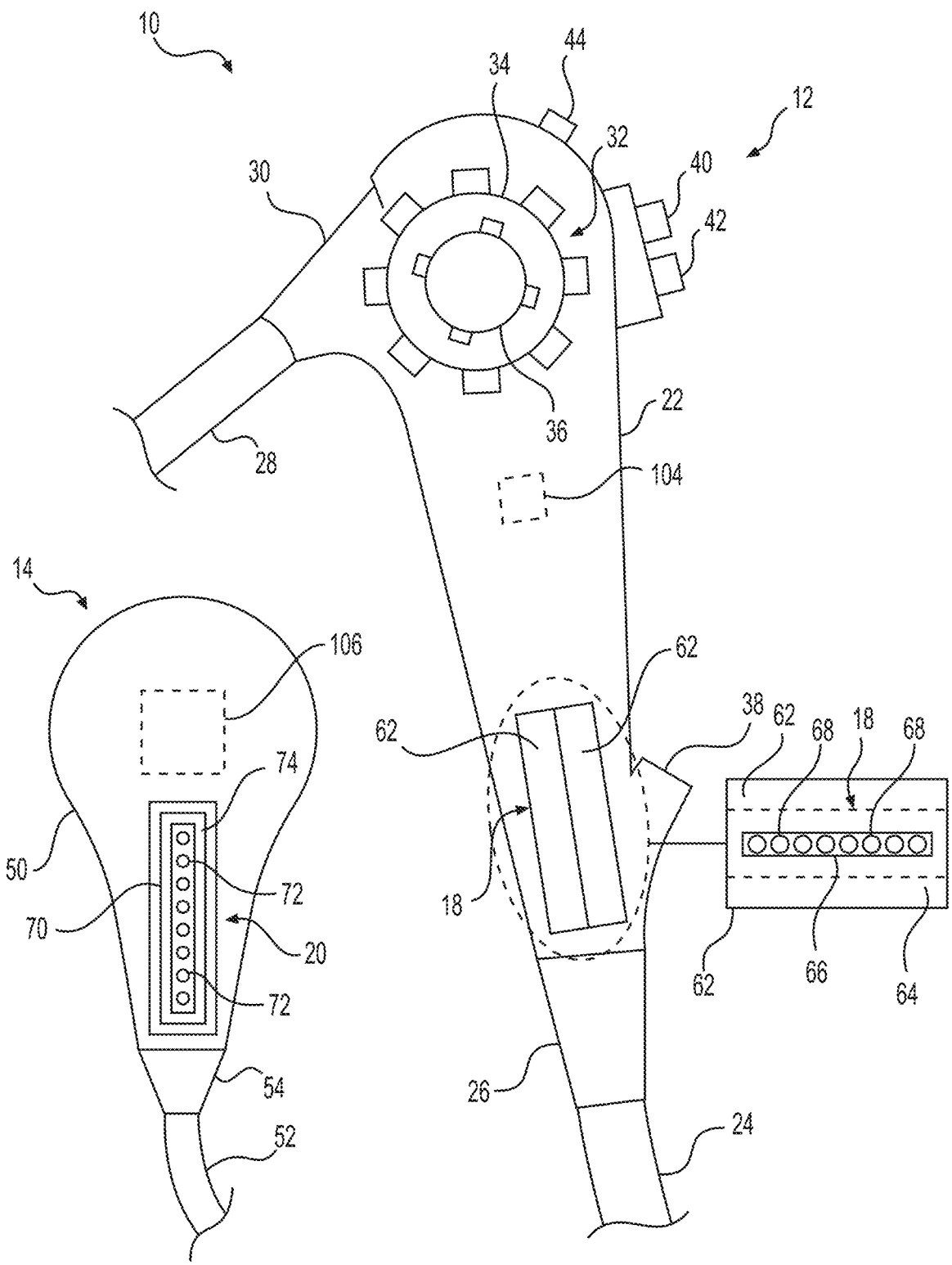
FIG. 2 illustrates the exemplary medical system of FIG. 1 in an uncoupled configuration, according to aspects of the present disclosure.

FIGS. 1 and 2 depict a medical system 10 that includes an insertion device 12 and a medical device 14. FIG. 1 illustrates insertion device 12 and medical device 14 in a coupled configuration, and FIG. 2 illustrates insertion device 12 and medical device 14 in an uncoupled configuration. FIG. 1 shows a first side of medical device 14, and FIG. 2 shows a second side of medical device 14, opposite to the first side. Insertion device 12 may be an endoscope, duodenoscope, bronchoscope, ureteroscope, colonoscope, or other type of medical device. In one aspect, insertion device 12 may be a single-use type medical device. In another aspect, insertion device 12 may be a reusable type medical device. Medical device 14 may be a catheter with one or more illumination devices (e.g., LEDs) and one or more visualization devices (e.g., a camera), for example, a SpyScope™ device manufactured and sold by Boston Scientific Corporation. Insertion device 12 and medical device 14 may be physically and electronically coupled via a connection 16 formed by a connector 18 on insertion device 12 and a connector 20 on medical device 14, as shown in FIG. 2.

Figure 3:
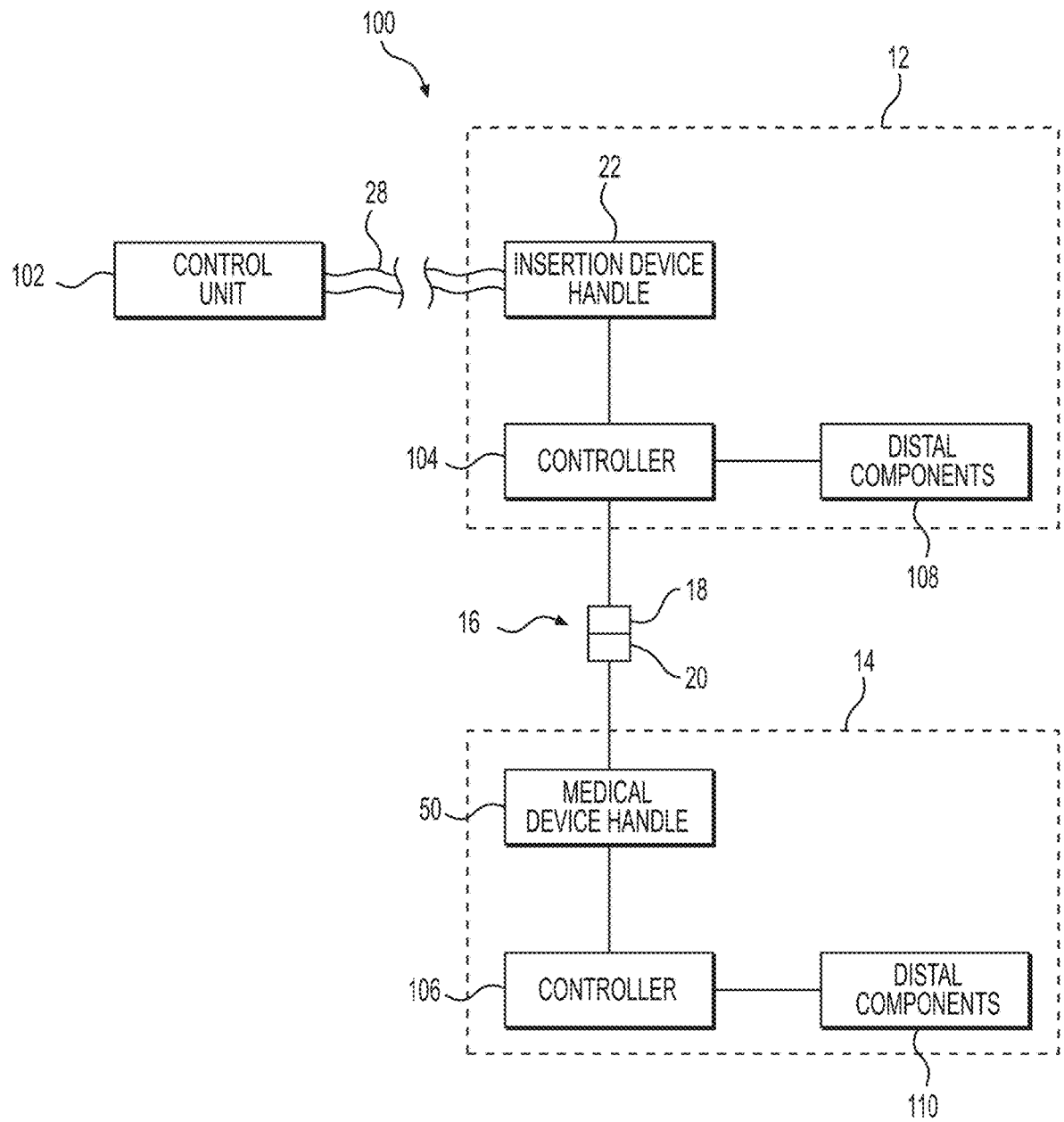
FIG. 3 is a schematic view of a control system for at least a portion of the exemplary medical system of FIGS. 1 and 2, according to aspects of the present disclosure.

Insertion device 12 may have a handle portion 22 and an insertion portion 24, which may be inserted into a body lumen of a subject during a medical procedure. Insertion portion 24 may be joined to handle portion 22. A stress relief portion 26 may bridge handle portion 22 and insertion portion 24. An umbilicus 28 may extend from handle portion 22, and another stress relief portion 30 may bridge handle portion 16 and umbilicus 28. As shown in FIG. 3, umbilicus 28 may be used to connect insertion device 12 to components or capital equipment, such as a control unit (for providing, e.g., optical controls including camera, video, light, or other optical controls), an air and/or water supply, and/or a suction supply.

Handle portion 22 may include a number of components used by an operator to control insertion device 12 before, during, or after a procedure involving insertion device 12. For example, handle portion 22 may include steering components 32. Steering components 32 may be used to control deflection of a distal portion (not shown) of insertion portion 24. Steering components 32 may be a part of a steering assembly. For example, steering components 32 may include two knobs 34, 36 used for deflecting a distal portion of insertion portion 24. One of knobs 34, 36 may be used to deflect a distal portion of insertion portion 24 along a first axis, and the other of knobs 34, 36 may be used to deflect the distal portion of insertion portion 24 along a second axis transverse to the first axis. For example, knob 34 may be operable to deflect a distal portion of insertion portion 20 in a left/right direction, and knob 36 may be operable to deflect a distal portion of insertion portion 24 in an up/down direction. Although not shown, steering components 32 may also include one or more locking mechanisms, which may be used to limit a distal portion of insertion portion 24 from moving in a left/right and/or up/down direction or otherwise lock the position of the distal portion of insertion portion 24.

Insertion device 12 may also include a number of ports and/or valves. For example, handle portion 22 may include a working channel port 38 that may be used for passing one or more instruments or other devices (e.g., a portion of medical device 14) through a working channel of insertion portion 24 to the distal end of insertion device 12. Working channel port 38 may include a valve to prevent leakage. Insertion device 12 may also include fluidics components, such as valves 40, 42 for providing air, water, and/or suction. Valves 40, 42 may connect to tubing in umbilicus 28, handle portion 22, and/or insertion portion 24, such that pressing on or otherwise actuating valves 40, 42 permits the corresponding function. For example, valve 40 may be used to provide air and/or water through one or more lumens of insertion portion 24, and valve 42 may be used to provide suction and may connect to one or more lumens of insertion portion 24. Insertion device 12 may also include other components such as elevator lever 44, which may be used to move an elevator (not shown) at a distal end of insertion portion 24 up and/or down. For example, elevator lever 44 may be used where insertion device 12 is a duodenoscope.

Furthermore, a distal end of insertion portion 24 may include one or more distal components 108 (FIG. 3), for example, illumination devices (e.g., LEDs), one or more visualization devices (e.g., cameras), etc. The one or more distal components 108 may be coupled to a controller 104 within handle portion 22 of insertion device 12 and to a control unit 102.

Medical device 14 may include a handle portion 50 and an insertion portion 52. As shown in FIG. 1, handle portion 50 may be coupled to handle portion 22 of insertion device 12 via connection 16. Insertion portion 52 be inserted through working channel port 38 and through insertion portion 24 of insertion device 12 such that insertion portion 52 may extend through and distally beyond a distal end tip of insertion portion 24 and into the body of a subject during a medical procedure. Insertion portion 52 may be joined to handle portion 50. A stress relief portion 54 may bridge handle portion 50 and insertion portion 52.

Handle portion 50 may include a number of components used by an operator to control insertion device 52 before, during, or after a procedure involving insertion device 52. For example, handle portion 50 may include steering components 56. Steering components 56 may be used to control deflection of a distal portion (not shown) of insertion portion 52. Steering components 56 may be a part of a steering assembly. For example, steering components 56 may include two knobs 58, 60 used for deflecting a distal portion of insertion portion 24. One of knobs 58, 60 may be used to deflect a distal portion of insertion portion 52 along a first axis (e.g., a left/right direction), and the other of knobs 58, 60 may be used to deflect the distal portion of insertion portion 52 along a second axis transverse to the first axis (e.g., a up/down direction), as discussed above with respect to insertion device 12. Although not shown, steering components 56 may also include one or more locking mechanisms, which may be used so as to limit a distal portion of insertion portion 52 from moving in a left/right and/or up/down direction or otherwise lock the position of the distal portion of insertion portion 52. Although not shown, medical device 14 may include a number of ports and/or valves.

Furthermore, a distal end of insertion portion 52 may include one or more distal components 110 (FIG. 3), for example, illumination devices (e.g., LEDs), one or more visualization devices (e.g., cameras), etc. The one or more distal components 110 may be coupled to a controller 106 within handle portion 50 of medical device 14, to a controller 104 within handle portion 22 of insertion device 12, and to a control unit 102.

As mentioned above, insertion device 12 and medical device 14 may be coupled via connection 16. Insertion device 12 includes connector 18, and medical device 14 includes connector 20. Connector 18 may be positioned on an intermediate position on handle portion 22, for example, proximal of stress relief portion 26 and distal to steering components 32. Similarly, connector 20 may be positioned on an intermediate position on handle portion 50, for example, proximal of stress relief portion 54 and distal to steering components 56. In one aspect, connector 18 may be a female connector, and connector 20 may be a male connector. In another aspect, connector 18 may be a male connector, and connector 20 may be a female connector.

As shown in FIG. 2, connector 18 of insertion device 12 may include one or more movable doors 62 to form a cover and a recessed port 64. The one or more movable doors 62 may be pivotably coupled to edges of recessed port 64, for example, on opposite sides of recessed port 64. The one or more movable doors 62 may be biased to block recessed port 64, but may be pivotable to expose or otherwise provide access to recessed port 64. Movable doors 62 may provide ingress protection for recessed port 64 when medical device 14 is not connected to insertion device 12, for example, during a different procedure, during positioning of insertion device 12, or before the medical procedure. Recessed port 64 includes a connection portion 66, which may include one or more pin holes 68. Connection portion 66 may extend outward from recessed port 64 to form the one or more pin holes 68. Pin holes 68 may be electronically connected to controller 104.

Although not shown, in another aspect, connector 18 of insertion device 12 may include a breakaway covering or a tear away covering. For example, the breakaway covering or tear away covering may be punctured or removed when connector 20 of medical device 14 is inserted into or otherwise coupled to connector 18 of insertion device 12. The breakaway covering or tear away covering may be used in addition to movable doors 62 or without movable doors 62. In this aspect, the breakaway covering or tear away covering may help protect recessed port 64 or other components of connector 20. Additionally, the breakaway covering or tear away covering may also help to indicate whether insertion device 12 has previously been coupled to and/or used with a medical device.

Connector 20 of medical device 14 may include a connection portion 70 that includes one or more pins 72. Pins 72 may be electronically connected to controller 106. The one or more pins 72 may be configured to be received within corresponding pin holes 68 to form an electronic connection between controller 104 and controller 106. Additionally, although eight pins 72 and eight pin holes 68 are shown in FIG. 2, this disclosure is not so limited, as connector 20 and connector 18 may include any number of pins, pin holes, or other connection elements. In one aspect, connector 18 may include six pin holes 68, and connector 20 may include six pins 72.

Connection portion 70 may include one or more extension portions 74 that may surround but be spaced away from pins 72. Extension portions 74 may extend farther away from handle portion 50 than pins 72, for example, to protect pins 72 during coupling with insertion device 12 and/or to help open movable doors 62 to allow pins 72 to be coupled to pin holes 68. Additionally, extension portions 74 may be configured to abut and surround connection portion 66 of connector 18 on insertion device. For example, coupling connector 20 to connector 18 may form a friction fit between extension portions 74 and connection portion 66 to physically couple medical device 14 to insertion device 12.

In one aspect, the amount of force required to disconnect connector 18 and connector 20 may be greater than (e.g., approximately two times greater than) the forces that may be imparted to insertion device 12 and medical device 14 during a medical procedure. As such, connector 18 and connector 20 may help to ensure that medical device 14 is only disconnected from insertion device 12 by a user or other medical professional after a medical procedure is completed, when a portion of the medical procedure necessitates disconnection, or otherwise when intended.

Although FIG. 2 and the discussion above discloses insertion device 12 including pin holes 68 and medical device 14 including pins 72 such that medical device 14 plugs into a socket in insertion device 12, this disclosure is not so limited. For example, insertion device 12 may include pins, and medical device 14 may include pin holes. Alternatively, insertion device 12 and medical device 14 may be physically and electronically connected via one or more other techniques. Additionally, as discussed below with respect to FIG. 4, connector 18 and connector 20 may include one or more contoured shapes to help securely and releasably connect medical device 14 to insertion device 12 such that the connection is maintained during manipulation of one of more of insertion device 12 and medical device 14 during the medical procedure.

As shown in FIG. 3, various components of insertion device 12 and medical device 14 may be coupled to form a control system 100. Control system 100 includes a control unit 102. Control unit 102 may be a capital box (e.g., capital equipment) with one or more of a user interface, display, etc. Control unit 102 may be coupled to insertion device 12 via umbilicus 28. With insertion device 12 and medical device 14 coupled via connection 16, control unit 102 may deliver power and provide a ground to both insertion device 12 and medical device 14 via umbilicus 28. Additionally, control unit 102 may also receive and transmit information and signals to and from both insertion device 12 and medical device 14 via umbilicus 28 in order to perform a two-way digital communication. For example, control unit 102 may be coupled to a controller 104 within insertion device 12 (e.g., within handle portion 22). Additionally, control unit 102 may be coupled to a controller 106 within medical device 14 (e.g., within handle portion 50). In this aspect, controller 106 may be coupled to controller 104 via connection 16, such that controller 106 within medical device 14 is indirectly coupled to control unit 102 via controller 104 within insertion device 12. In another aspect, one or more of insertion device 12, medical device 14, or control unit 102 may provide an indication or signal a verification that insertion device 12 and medical device 14 are compatible, that one or more of insertion device 12 and medical device 14 are suitable for a medical procedure, etc.

Control unit 102 may receive signals from distal components 108 of insertion device 12 and from distal components 110 of medical device 14. In one aspect, controller 104 may perform a digital modulation to consolidate video signals from insertion device 12 and from medical device 14 into a single conductive medium. For example, umbilicus 28 may include a single coaxial cable. In this aspect, video signals from insertion device 12 may be transmitted on one channel, and video signals from medical device 14 may be transmitted on another channel.

In one example, control unit 102 may include an 8-pin connection with umbilicus 28. Two pins may provide an inter-integrated circuit to drive distal components 108 and 110 (e.g., LEDs). Four pins may provide two lines of high-speed signal communication, and two pins may provide a power and a ground. Accordingly, the inter-integrated circuit, high-speed signal communication, power, and the ground may connect control unit 102 to controller 104 in insertion device 12. In one example, connector 18 and connector 20 may include a six pin connection. In this aspect, two pins may provide an inter-integrated circuit to drive distal components 110 (e.g., LEDs) of medical device 14. Two pins may convey clock or timing information and data, respectively, for example, from an imaging unit at the distal end of medical device 14. Lastly, two pins may be dedicated for power and ground. In this aspect, controller 104 in insertion device 12 may perform a demodulation or compression procedure to allow for information from both insertion device 12 and medical device 14 to be delivered to control unit 102, while control unit 102 also provides information, power, ground, etc. to both insertion device 12 and medical device 14.

Furthermore, the digital modulation may utilize quadrature amplitude modulation ("QAM"). For example, the digital modulation may utilize a 64-QAM carrier, which may allow for a single wave to represent six bits of data by manipulating the amplitude and the phase of the wave into one of sixty-four different discrete states. Alternatively, the digital modulation may include orthogonal frequency division multiplexing ("OFDM"). OFDM may utilize multiple subcarriers to transmit the information from a single source, which may reduce signal noise and provide a high data rate throughput for wideband applications. In this aspect, OFDM may allow one set of subcarriers to transmit information from the distal components 108 of insertion device 12 and another set of subcarriers to transmit information from the distal components 110 of medical device 14. Moreover, other digital modulation or data compression techniques may be employed. In any of these aspects, the digital modulation or data compression may help to consolidate the information signals from insertion device 12 and medical device 14, and may help reduce the required size for umbilicus 28 and the required number of connection pins and/or components to couple umbilicus 28 to controller 102, thus reducing the complexity and/or cost of umbilicus 28 and the other components of control system 100.

Although the above discussion includes the demodulation and/or compression being performed by controller 104 of insertion device 12, this disclosure is not so limited. For example, in one aspect, controller 106 of medical device 14 may demodulate and/or compress signals from distal components 110 of medical device 14, and controller 104 of insertion device 12 may demodulate and/or compress signals from distal components 108 of insertion device 12.

Figure 4:
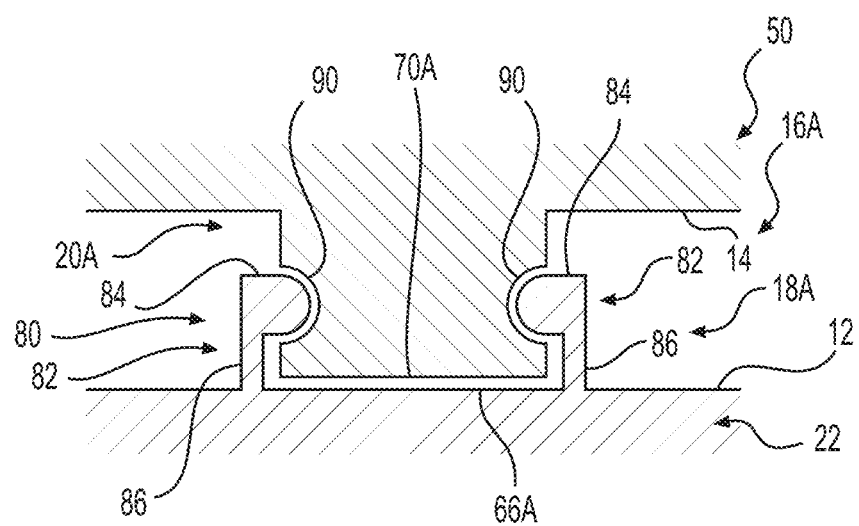
FIG. 4 illustrates an alternative configuration of a portion of the exemplary medical system of FIGS. 1 and 2.

FIG. 4 illustrates an exemplary locking mechanism 80 that may be used to releasably couple an exemplary connector 18A of insertion device 12 to an exemplary connector 20A of medical device 14. It is noted that the pins and pin holes, discussed above, are omitted in FIG. 4 for clarity. Locking mechanism 80 may include two prongs 82 that extend away from insertion device 12. Prongs 82 may include widened end portions 84 and arms 86 connected to handle portion 22 of insertion device 12. Additionally, connector 20A of medical device 14 may include indentations 90 that may align with widened end portions 84 to couple connector 20A to connector 18A.

In order to couple connector 20A to connector 18A, connection portion 70A of connector 20A may be extended toward handle portion 22 of insertion device 12, for example, toward connection portion 66A of connector 18A. Connection portion 70A may interact with widened end portions 84 and force arms 86 to flex, or bend outward. Further movement of connection portion 70A may provide for widened end portions 84 aligning with indentations 90, and further provide for arms 86 to return to their normal, relaxed, non-bent positions. With widened end portions 84 and indentations 90 aligned, insertion device 12 and medical device 14 may be coupled such that forces required to bend arms 86 outward and remove connection portion 70A away from handle portion 22 of insertion device 12 may be greater than forces that may be imparted to insertion device 12 and medical device 14 during a medical procedure, as discussed above. Arms 86 and indentations 90 may have curved or angled shapes, which may help in the coupling or uncoupling of medical device 14 and insertion device 12. Furthermore, arms 86 may be manually bent outward by the user in order to assist in coupling or uncoupling medical device 14 and insertion device 12. It is understood that medical system 10 may include any fastening mechanism for releasably attaching insertion device 12 and medical device 14, e.g., including corresponding features for engagement/disengagement.

Although locking mechanism 80 is shown as being a part of insertion device 12, this disclosure is not so limited. For example, a locking mechanism may extend from medical device 14 and may be releasably secured to a portion of insertion device 12. Moreover, in another aspect, locking mechanisms may extend from both insertion device 12 and from medical device 14, which may be releasably secured to a portion of medical device 14 and insertion device 12, respectively. Alternatively or additionally, medical system 10 may include one or more other coupling features in order to releasably physically and electronically couple medical device 14 to insertion device 12.

Figure 5:
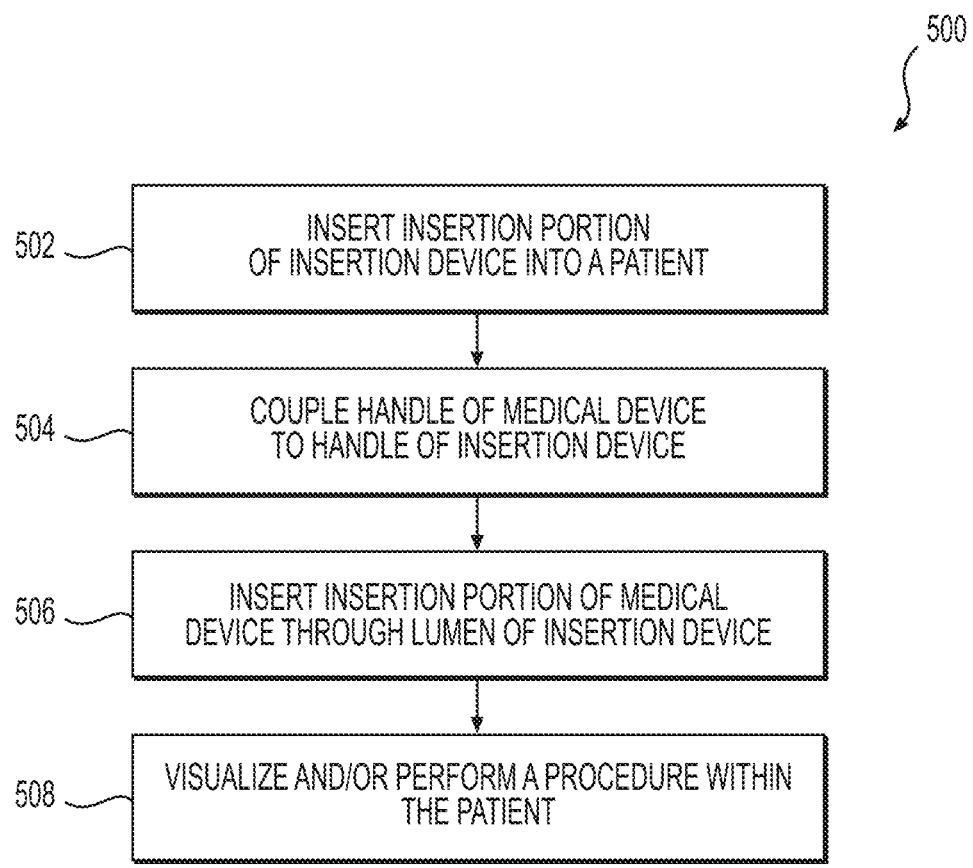
FIG. 5 is a flow diagram of an exemplary treatment method, according to aspects of the present disclosure.

FIG. 5 is a flow diagram portraying an exemplary treatment method 500 to treat or visualize a body lumen of a patient. Method 500 includes a step 502, wherein the user inserts or positions insertion portion 24 of insertion device 12 within the patient. Step 502 may include a preliminary step of coupling insertion device 12 to capital equipment, for example, control unit 102, via umbilicus 28. Step 502 may also include visualizing an internal portion of the patient with one or more distal components 108 (e.g., illumination and/or imaging devices) at a distal end of insertion portion 24. Additionally, step 502 may include maneuvering insertion portion 24 via one or more of steering components 32.

In a step 504, the user may couple handle portion 50 of medical device 14 to handle portion 22 of insertion device 12. For example, connector 20 or connector 20A of medical device 14 may be coupled to connector 18 or connector 18A, respectively, of insertion device 12. Additionally, coupling medical device 14 to insertion device 12 may include physically and electronically connecting medical device 14 to insertion device 12. As discussed above, the connection may be friction fit (FIGS. 1 and 2), may include a contoured and biased engagement (FIG. 4), or another releasable coupling mechanism.

In a step 506, insertion portion 52 of medical device 12 may be inserted through a lumen of insertion device 12. For example, insertion portion 52 may be inserted through port 38 in handle portion 22 and through insertion portion 24. In one aspect, insertion portion 52 of medical device 12 may be delivered to a position aligned with the distal end of insertion portion 24 of insertion device 12. In another aspect, insertion portion 52 of medical device 12 may be delivered to a position distally beyond the distal end of insertion portion 24 of insertion device 12. In this aspect, a distal end of insertion portion 52 may be controlled via steering components 56. In either aspect, the position of the distal end of insertion portion 52 of medical device 14 relative to the distal end of insertion portion 22 of insertion device 12 may be controlled via the position of insertion portion 52 relative to port 38. Stated another way, insertion portion 52 may be threaded or inserted distally through port 38 to extend the distal end of insertion portion 52 relative to the distal end of insertion portion 22 of insertion device 12. Insertion portion 52 may also be retracted proximally out of port 38 to withdraw the distal end of insertion portion 52 relative to the distal end of insertion portion 22 of insertion device 12.

Next, a step 508 may include visualizing and/or performing a procedure within the patient. The visualizing and/or performing the procedure may include visualizing, treating, and/or otherwise manipulating tissue or other material within the patient. For example, the user may utilize one of distal components 108 of insertion device 12 or distal components 110 of medical device 14 to illuminate and/or to visualize an internal portion of the patient. In one aspect, insertion portion 22 of insertion device 12 may be used to access and/or visualize the papilla, for example, in step 502, and insertion portion 52 of medical device 14 may be extended to access and/or visualize the biliary duct of a subject, for example, in step 508. Additionally, signals from distal components 108 or distal components 110 may be transmitted through umbilicus 28 to control unit 102 to be analyzed, stored, displayed, etc. Moreover, insertion device 12 and/or medical device 14 may include one or more additional medical components (e.g., electrodes, graspers, knives, etc.) in order treat tissue or other material within the cavity.

The aforementioned aspects may allow medical device 14 to be directly coupled to insertion device 12 to form a releasable physical and electronic connection. As a result, insertion device 12 may be coupled to control unit 102 via umbilicus 28 without the need for medical device 14 to be coupled to control unit 102 or another control unit, thus reducing the number of cables or wires for medical system 10. Doors 62 or other elements may help provide a hinged cover for ingress protection for connector 18 on insertion device 12. The respective sizes and arrangements of connector 18 and connector 20 may help form a friction coupling to secure medical device 14 to insertion device 12 via an integrated locking mechanism. Additionally or alternatively, one or more of insertion device 12 and medical device 14 may include a locking mechanism 80, as discussed with respect to FIG. 4.

One or more of the aforementioned aspects may allow for insertion device 12 and medical device 14 to be powered by a single power source, for example, within control unit 102, via a single umbilicus 28. Control unit 102 may provide power to both insertion device 12 and medical device 14. The power may be sufficient to power illumination devices (e.g., LEDs), visualization devices (e.g., cameras), and other elements on both insertion device 12 and medical device 14. Moreover, one or more of the aforementioned aspects may allow for output signals, for example, video output, from one or more distal components 108 on insertion device 12 and distal components 110 on medical device 14 to be output to control unit 102 and, for example, displayed on a monitor, via a single umbilicus 28. Furthermore, one or more of the aforementioned aspects may allow for insertion device 12 and medical device 14 to be securely and releasably coupled to each other without the need for any additional coupling mechanisms. Accordingly, insertion device 12 and medical device 14 may be powered and configured to transmit information during a medical procedure with a reduced number of cables or wires, improving usability during a medical procedure. Additionally, insertion device 12 and medical device 14 may be held and/or maneuvered together without requiring additional coupling mechanisms.

Medical system 10, control system 100, and method 500 may be used to perform any of the above procedures, without the need for an additional umbilicus, wires, cables, etc., which may reduce the overall procedure time, component costs, and/or reduce the risks to the subject.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
a handle;
an insertion portion;
a distal component coupled to a distal end of the insertion portion;
a connection portion configured to electronically and physically couple the medical device to an insertion device;
a controller configured to be electronically coupled to a controller of the insertion device, wherein the controller of the medical device is configured to transmit signals from the distal component of the medical device to the controller of the insertion device; and
an umbilicus configured to indirectly couple the medical device to a control unit, wherein the umbilicus physically and electronically couples the control unit to the insertion device, wherein the controller of the insertion device is configured to receive signals from the distal component of the medical device and receive signals from the distal component of the insertion device, and wherein the control unit delivers power through the umbilicus to power the distal component of the medical device.

2. The medical device of claim 1, wherein the distal component of the medical device includes at least one of an illumination device, a visualization device, or a combination thereof.

3. The medical device of claim 1, further comprising pins electronically connected to the controller of the medical device, wherein pins of the medical device is configured to be received in pinholes of the insertion device to form an electronic connection between the medical device and the insertion device.

4. The medical device of claim 1, wherein the controller of the medical device is disposed within the handle of the medical device.

5. The medical device of claim 1, wherein the control unit is configured to signal a verification that the insertion device and the medical device are suitable to perform a medical procedure.

6. A medical system comprising:
a medical device including a handle, an insertion portion, a connection portion, and a distal component;
an insertion device including a handle, a controller, an insertion portion, a connection portion, and a distal component; and
a control unit that is physically and electronically coupled to the insertion device via an umbilicus, wherein the control unit delivers power through the umbilicus to power the distal component of the insertion device and to power the distal component of the medical device, wherein the connection portion of the medical device is configured to be coupled to the connection portion of the insertion device to form an electronic and physical connection between the insertion device and the medical device, wherein the controller of the insertion device is configured to receive signals from the distal component of the medical device and to transmit signals from the distal component of the medical device to the control unit.

7. The medical system of claim 6, further comprising:
a locking mechanism configured to releasably couple the medical device and the insertion device, wherein the locking mechanism includes:
  at least one prong formed in one of the connection portion of the medical device or the connection portion of the insertion device, and
  at least one indentation formed in another one of the connection portion of the medical device or the connection portion of the insertion device,
wherein the at least one indentation is configured to receive the at least one prong therein to releasably couple the medical device and the insertion device.

8. The medical system of claim 6, wherein the controller of the insertion device is configured to perform at least one of a demodulation operation or a compression operation on received signals from the distal component of the medical device, and to transmit signals to the control unit corresponding to at least one output from the demodulation operation or the compression operation.

9. The medical system of claim 6, wherein the distal component of the insertion device is coupled to a distal end of the insertion portion of the insertion device.

10. The medical system of claim 6, wherein the distal component of the insertion device includes an illumination device.

11. The medical system of claim 6, wherein the distal component of the insertion device includes a visualization device.

12. The medical system of claim 6, wherein the connection portion of the insertion device and the connection portion of the medical device are releasably coupled via a locking mechanism.

13. The medical system of claim 6, wherein the insertion device includes a port coupled to the insertion portion of the insertion device, wherein the port of the insertion device is configured to receive the insertion portion of the medical device therein.

14. The medical system of claim 13, wherein the insertion portion of the medical device extends distally beyond a distal tip of the insertion portion of the insertion device.

15. The medical system of claim 6, wherein the controller of the insertion device is configured to transmit signals from the distal component of the insertion device to the control unit.

16. The medical system of claim 6, wherein the medical device further includes a controller electronically connected to the controller of the insertion device.

17. The medical system of claim 16, wherein the connection portion of the insertion device includes pinholes electronically connected to the controller of the insertion device, wherein the connection portion of the medical device includes pins electronically connected to the controller of the medical device, and wherein the pinholes of the insertion device are configured to receive the pins of the medical device to form an electronic connection between the controller of the insertion device and the controller of the medical device.

18. The medical system of claim 16, wherein the controller of the medical device is disposed within the handle of the medical device.

19. The medical system of claim 6, wherein the controller of the insertion device is disposed within the handle of the insertion device.

20. The medical system of claim 6, wherein the control unit is configured to signal a verification that the insertion device and the medical device are suitable to perform a medical procedure.

* * * * *